(12) United States Patent
Klapproth et al.

(10) Patent No.: US 11,644,459 B2
(45) Date of Patent: May 9, 2023

(54) METHOD FOR SELECTING BIOLOGICAL BINDING MOLECULES

(71) Applicant: AVA LIFESCIENCE GMBH, Denzlingen (DE)

(72) Inventors: Holger Klapproth, Freiburg (DE); Marcus Dühren-Von Minden, Müllheim (DE)

(73) Assignee: AVA LIFESCIENCE GMBH, Denzlingen (DE)

( * ) Notice: Subject to any disclaimer, the term of this patent is extended or adjusted under 35 U.S.C. 154(b) by 24 days.

(21) Appl. No.: 17/414,788

(22) PCT Filed: Dec. 19, 2019

(86) PCT No.: PCT/EP2019/086450
§ 371 (c)(1),
(2) Date: Jun. 16, 2021

(87) PCT Pub. No.: WO2020/127827
PCT Pub. Date: Jun. 25, 2020

(65) Prior Publication Data
US 2022/0057396 A1 Feb. 24, 2022

(30) Foreign Application Priority Data
Dec. 20, 2018 (EP) .................................... 18000989

(51) Int. Cl.
G01N 33/50 (2006.01)
G01N 33/566 (2006.01)
G01N 33/569 (2006.01)
G01N 33/574 (2006.01)
G01N 33/68 (2006.01)

(52) U.S. Cl.
CPC ....... *G01N 33/5052* (2013.01); *G01N 33/566* (2013.01); *G01N 33/56972* (2013.01); *G01N 33/57484* (2013.01); *G01N 33/6854* (2013.01)

(58) Field of Classification Search
CPC ......... G01N 33/56972; G01N 33/5052; G01N 33/57484; G01N 33/6854
See application file for complete search history.

(56) References Cited

U.S. PATENT DOCUMENTS 9,926,381 B2 * 3/2018 Welt .................. C07K 16/4283

FOREIGN PATENT DOCUMENTS

| CN | 107109369 A | 11/2015 |
|---|---|---|
| CN | 108884143 A | 3/2017 |
| CN | 108794642 A | 7/2018 |
| EP | 1001020 A1 | 5/2000 |
| EP | 3543697 A1 | 9/2019 |
| WO | 2016079333 | 5/2016 |
| WO | 2017158116 | 9/2017 |

OTHER PUBLICATIONS

Hwang et al. (Related Mechanisms of Antibody Somatic Hypermutation and Class Switch Recombination . . . Microbiol Spectr 3 (1): 1-34 (Feb. 2015).*
Marcus Dühren-Von Minden et al., "Chronic lymphocytic leukaemia is driven by antigen-independent cell-autonomous signalling," Nature, vol. 489, No. 7415, Aug. 12, 2012.
Bojarczuk Kamil et al., "B-cell receptor signaling in the pathogenesis of lymphoid malignancies," Blood Cells, Molecules and Diseases, vol. 55, No. 3, Jul. 11, 2015.
Gur Yaari et al., "Practical guidelines for B-cell receptor repertoire sequencing analysis," Genome Medicine, vol. 7, No. 1, Nov. 20, 2015.
International Search Report, PCT/EP2019/086450, EPO, Rijswijk, NL, dated Mar. 24, 2020.

* cited by examiner

*Primary Examiner* — Gailene Gabel
(74) *Attorney, Agent, or Firm* — Saffire IP; Daren P. Nicholson

(57) ABSTRACT

The present invention relates to the field of producing, identifying, and selecting biological binding molecules, e.g. in particular antibodies or fragments thereof, which selectively bind to somatically hypermutated B-cell receptors or B-cell receptor complexes. The method is used in order to select a biological binding molecule which specifically binds to a B-cell receptor having hypermutated regions as the target receptor, but not to a B-cell receptor without hypermutated regions, and is carried out in a cell-based system using immature B cells which are in the pro/pre stage and cause a 'Triple Knockout' of the genes for RAG2 or RAG1, Lambda5, and SLP65.

15 Claims, No Drawings
Specification includes a Sequence Listing.

METHOD FOR SELECTING BIOLOGICAL BINDING MOLECULES

The instant application contains a Sequence Listing, which has been submitted electronically in ASCII format and is hereby incorporated by reference in its entirety. Said ASCII copy, created on Nov. 4, 2021, is named 32501-301301-Substitute_Sequence_Listing and is 11,212 bytes in size.

The present invention relates to the field of producing, identifying, and selecting biological binding molecules, e.g. in particular antibodies or fragments thereof, which selectively bind to somatically hypermutated B-cell receptors or B-cell receptor complexes.

In biochemistry, a protein or a protein complex is referred to as a receptor (from the Latin word "recipere": "to receive" or "to obtain") if signal molecules can bind thereto, which molecules are able to trigger signal processes inside the cell through the binding event. A receptor can receive signals from outside and can be located on the surface of a biomembrane, or it can be detectable in the cytosol of the cell. Receptors have a specific binding site for their physiological agonist or antagonist (binding partner, ligand).

Membrane receptors are located on the surface of biomembranes and consist of proteins that are often modified (e.g., carbohydrate chains). They have a specific fit for small molecules, so-called ligands, or for parts of larger molecules that bind to the receptor structure by adding to it as a complementary structure (simply called the "lock and key principle").

Receptors can thus serve to receive and transmit signals (signal transduction), or functionally participate in the cohesion of cells (cell adhesion) or the transport of substances into the cell (membrane transport). Furthermore, they can offer virions the possibility of docking with the appropriate host cell and infecting them.

The membrane receptors that are important for cell contacts include both cell adhesion molecules that mediate cell-cell contacts such as cadherins, selectins, and immunoglobulins, as well as those that are involved in the formation of cell-matrix contacts and anchor cells to the extracellular matrix such as the integrins.

Membrane receptors are not only found on the plasma membrane, but also on biomembranes of the organelles inside the cell. While external cell membrane receptors relate the cell to the external space as the environment thereof, in the interior of the cell individual organelles are related to the cytoplasm, cytoskeleton, or to one another via receptors.

Receptors in the cell membrane are divided into ionotropic and metabotropic receptors according to their mode of action.

Ionotropic receptors are ion channels that are more likely to open when a suitable ligand binds, thereby changing the conductivity of the membrane.

Metabotropic receptors, on the other hand, do not form channels or pores, but instead activate a downstream "second messenger" (e.g., a G protein or a protein kinase) when their ligand binds and thus modulate intracellular signal cascades through changes in the concentration of secondary messenger substances, which, however, can also indirectly result in a change of the membrane permeability.

For many receptors there are natural ligands that activate these receptors and trigger a 'second messenger' cascade. In addition to natural ligands, there are also substances that bind to the receptor and either activate it (agonists) or inactivate it (antagonists). Examples of receptor agonists are antigens including allergens, opioids, nicotine, salbutamol, muscarine, cytokines, and neurotransmitters.

A special receptor in this regard is the B-cell receptor or B-cell receptor complex (BCR). This BCR is expressed by B cells and represents a kind of membrane-bound antibody.

The BCR is produced in great variety in maturing B cells. Usually this BCR is of the IgD or IgM type.

In humans and also in some other mammals, the development of the B cells takes place in the bone marrow or in the fetal liver. The signals that are necessary for the development program are received by the developing lymphocytes from so-called stromal cells. In B-cell development, the formation of a functioning B-cell receptor (the membrane-bound form of the "antibody") is of crucial importance. Only with this antigen receptor are mature B cells later able to recognize foreign antigens and to bind to hostile structures through the formation of appropriate antibodies. The antigen specificity of the receptor is determined by linking specific gene segments. The segments are called V, D, and J segments, which is why the process is known as V(D)J recombination. In the process, these segments, which form the antigen-binding part of the B-cell receptor, are rearranged. The entire receptor consists of two identical light protein chains and two identical heavy protein chains, the heavy and light chains being linked to one another via disulfide bridges. In VDJ recombination, first the V, D, and J segments of the heavy chain of the B-cell receptor are linked, then the V and J segments of the light receptor chain. Only when the genes are successfully rearranged, which is known as productive gene rearrangement, the cell can move on to the next development step.

B cells that react to the body's own antigens during their maturation in the bone marrow die in the vast majority of cases as a result of apoptosis. Small amounts of autoreactive cells, including those against thyroglobulin or collagen, can be detected in the blood of healthy people (Abul K. Abbas: *Diseases of Immunity* in Vinay Kumar, Abul K. Abbas, Nelson Fausto: *Robbins and Cotran—Pathologic Basis of Disease*. 7th Edition. Philadelphia 2005, pp. 224f).

The insertion of mutations into the antibody genes of a maturing B cell is called somatic hypermutation. This event takes place in follicular B cells. Somatic hypermutation is the process a B cell goes through to reach the affinity matured state. It is an important step in the adaptive immune system. Random changes in the DNA occur with the help of the enzyme "activation induced cytidine deaminase" (AID or AICDA). AID deaminates cytosine in single-stranded DNA to form uridine. The enzyme UNG removes uracil and creates an abasic site. A single strand break is generated there by APE1. As a consequence, the cell-internal repair mechanism is activated in this way, whereby sequence changes are then randomly inserted during the repair. This can then lead to a structural change at the amino acid level and thus to a conditional change in the affinity of the B-cell receptor (BCR). This process ends when the affinity for the antigen has reached a specific strength via mechanisms that have not yet been clarified.

By selection, those cells are chosen which bind the antigen best and can therefore fight it most effectively. The remaining cells perish. This process, which takes place in the germinal centers of the secondary lymphatic organs (spleen, lymph nodes), allows the organism to produce a large number of different antibodies and thus to adapt to the pathogens that change in the course of immune evasion, as well as the affinity of the antibodies to increase antigen. This step results in the creation of unique B-cell populations, which are usually mono- or oligoclonal. If such a population is involved in a disease process with an autoimmune or malignant background (regardless of whether it is causal or supportive), the disease process can be positively influenced by removing these cells from the body, in that the disease-related symptoms are reduced or completely disappear. In order to selectively remove these B cells from the body, extremely specific antibodies are required. These can then be used, for example, as a membrane-bound receptor, as part of a chimeric receptor (for example using CAR-T cells), or as therapeutic antibodies in soluble form. Another application is a pretherapeutic apheresis, in which the matrix-bound antibody is used to separate the malignant cells from the blood. The tumor burden on the patient would be significantly reduced and the immune system would be burdened to a lesser extent by killing the remaining cells.

The removal of these specific B cells results in the fact that the immune system is not completely paralyzed as by killing all B cells and the previous immunities (e.g., after infections or vaccinations) are not cancelled, but it rather results in the fact that the patient still has an operational immune system despite therapy.

For the generation of antibodies against receptors, soluble versions of these receptors (in recombinant and purified form) are usually used for the immunization of mice. In rare cases, peptide fragments can also be used. Hybridoma cells are used to create antibody-producing hybridoma cells from the specific B cells that develop in the mouse.

These hybridoma cells produce antibodies which are then tested using ELISA or using expressed receptors in cell systems. Conventionally established cell lines are used for this purpose, since only these can easily be cultured. Antibodies can be generated that bind relatively specifically to a specific type of receptor (e.g., anti-IgG1, anti-IgE). However, this often results in cross-reactions with other receptors or other epitopes.

In general, for a therapeutic application of BCR antibodies, it is usually not sufficient to use only one antibody against the BCR since such broad-spectrum use can trigger considerable side effects. Rather, it would be desirable to provide an antibody which selectively binds to a receptor which has an activation such as, in particular, an undesired (pathophysiological or autonomous) activation. Such an antibody is not known in the prior art and there is no method for producing or obtaining it by selection.

The object of the invention is therefore to provide a system for the production or extraction and identification or selection of biological binding molecules such as, in particular, antibodies or functional fragments of the same, which bind highly selectively to affinity-matured BCRs, which are distinguished from the germline-encoded sequences of the BCR components by the hypersomatic mutations. This makes it possible to develop antibodies against disease-specific B cells, which can be used advantageously in the context of individualized therapy. In this case, it is important that the receptors or receptor complexes that are used in the context of the selection have correct folding and are therefore preferably functional.

According to a preferred embodiment, the functionality of the BCR is checked before it is used for selection. If the cells are induced with 4-OH tamoxifen before the measurement, the activation of the BCR can be detected by measuring the calcium signal (Dühren von Minden et al. 2012, Nature 489, p309-313). As a reference for the specific selection, a BCR is constructed which corresponds to the target BCR without the somatic hypermutations.

The object is achieved by providing a method according to the main claim. Preferred embodiments are the subject of corresponding subclaims.

Before the individual aspects of the present invention are discussed in detail, relevant terms that are used in the context of the present description are clarified.

B-cell receptors of the germline type—i.e. BCR, the amino acid sequence of which is encoded by gene sequences as they occur in the genome of the cell and thus correspond thereto—are generated by gene synthesis and represent a receptor type that is homologous to the somatically hyper-mutated receptors.

In the present case, "biological binding molecules" are understood to mean, for example, but not exclusively, antibodies including fusion proteins. Advantageously, and therefore preferably, such an antibody is selected from the group consisting of an IgG antibody, an IgM antibody, a humanized IgG antibody, and a human antibody into which the recognition sequence of the epitope is inserted. A binding molecule of this type can also be provided in the form of a functional fragment of the entire antibody, for example as a Fab fragment. A binding molecule can also include further regions which, for example, result in the killing/dying off of neoplasms and accordingly have the functionality of an immunotoxin and/or immunocytokine (e.g. "antigen drug conjugate," ADC). In particular, such a binding molecule can also be membrane-bound or cell-bound. Such a membrane-bound form of a binding molecule is, for example, the chimeric antigen receptor (CAR) on CAR-T cells. For diagnostic applications, the binding molecule can comprise detectable markings such as, in particular, one or more fluorescent dyes.

The task of the B-cell receptor complex (BCR) on the surface of a B cell is to recognize and bind pathogens. As already mentioned, this binding results in a change in conformation of the BCR, which triggers a signal cascade that ultimately results in an activation of the B cell. Since the process of generating such a BCR is based on a random aggregation of gene segments, it can happen that the newly created BCR undesirably recognizes the body's own structures and is thus undesirably "permanently activated." In order to prevent the development of such a "permanently active or activated" BCR, there are various protective mechanisms of the body. However, if these are overcome due to a pathological change in the developing B cell, a malignant or autoimmune disease can develop. In other cases, exposure to an antigen can result in the maturation of B cells with undesirable BCR properties.

During the maturation of the B cells, exposure of the B cells to the antigen results in an effect known as somatic hypermutation, in which the variability of the BCR in the germline is increased by enzymatic activity. Random changes in the DNA sequence of the BCR are inserted and selected. As a result, antibodies/BCRs with a higher binding strength to their epitope can be formed. This makes these antibodies/BCR unique. Since the somatic hypermutation(s) arise from an already functional BCR, this process can result in the formation of both monoclonal and oligoclonal B-cell populations. In these B cells, the amino acid sequence of the BCR forms a basis, which is varied by the mutations. These variations can now be selectively recognized by suitable binding molecules (antibodies and the fragments thereof). In this way, disease-associated B cells can be specifically recognized (if necessary diagnosed) and treated. A recognition as such can take place for example by means of flow cytometry. If a plurality of BCR variants that all have a common origin (i.e., are oligoclonal) are used, an antibody against oligoclonal BCR can also be obtained. In other words, a plurality of differently somatically hypermutated B-cell receptors in the form of oligoclonal derivatives of the same origin are used as target receptors in this case.

Therapy can take place, for example, by means of therapeutic antibodies (human or humanized antibodies, immunotoxins). The advantage of a therapy designed in this way is that only the disease-causing part of the B-cell population is recorded, whereby the systemic effects of the therapy that usually occur according to conventional therapeutic approaches can be minimized or even completely excluded.

In the course of the numerous experiments carried out for the present invention, however, it was surprisingly found that antibodies with particular specificity for these modified receptor regions (epitopes) cannot be produced and selected using customary standard methods. Only after the experimental conditions were adapted in such a way that genetically modified cells were used in the context of binding studies, the modified B-cell receptors of which were in a native and/or activated or activatable state, could suitable antibodies with the desired and required specificity be obtained. In other words, it is of substantial importance for the solutions proposed according to the invention that the cells used in binding studies for the selection of suitable prophylactic or therapeutic and diagnostic antibodies present their modified regions (epitopes) in a largely native and activatable form. It was found that so-called pro/pre B cells are particularly suitable due to their physiological constitution. The provision of such specific antibodies and functional fragments of the same, which also have this specific binding behavior, thus allows for disease-specific treatment that is characterized by a significantly improved treatment success and, by virtue of the reduction of undesirable systemic effects, by a significantly increased therapeutic success. In the context of diagnostic applications, the possibility of using such specific antibodies means a much more precise analysis with a much higher significance with regard to the evaluation of a patient's condition to be assessed.

The differentiation of B lymphocytes (B cells), for example in the mouse, can be subdivided into phases which are separate from one another and which can be further subdivided phenotypically and genotypically. The earliest B precursors (pro B cells) that can be found in the bone marrow of wild-type mice are derived from a pluripotent hematopoietic stem cell that does not express any cell line-specific markers, but which can be marked by the expression of the stem cell antigen 1 (Sca-1) on the surface thereof. In the transition from the pro B cell to the pre B cell, cells are generated that have $DJ_H$ rearrangements in the IgH chain (pro/pre B cells). The genes RAG1 and RAG2 are required for this gene rearrangement. At this stage, all other Ig gene loci are usually still in the germline (GL) configuration. Pre B cells with a $DJ_H$ rearrangement are called pre B-I cells and can be grown in tissue culture under specific conditions. The next rearrangement event in these cells involves the rearrangement of one of the $V_H$ gene segments with a pre-existing $DJ_H$ element. If this achieves a productive rearrangement of any allele so that a pH chain can be expressed, these cells receive a proliferative signal, whereby they multiply and differentiate into pre B-II cells. These cells can no longer express the surface marker c-kit, but acquire the ability to express CD25. Another productive rearrangement on any of the IgL alleles results in differentiation into immature B cells expressing membrane-bound immunoglobulins (IgM). These immature native B cells can leave the bone marrow and migrate to peripheral lymphoid organs, where they can eventually encounter antigens. In the course of an immune reaction, these B cells can differentiate into antibody-secreting plasma cells, during which a further DNA recombination process (class-switch recombination) can occur in the locus of the constant IgH region, which results in a change of the amount of antibody isotype secreted by the plasma cells. Some diseases are associated with B cells which, in addition to affinity maturation, have also undergone a so-called class-switch recombination (CSR).

A class-switch recombination (CSR or "isotype switching") refers to an isotype switch in the B cells of the immune system in immunology. In the course of an immune response, different isotypes of the immunoglobulins are needed on the B cells. By means of the class-switch recombination, B cells can change their antibody isotype. The VDJ sequence of the heavy chain switches from one C-region to another C-region arranged downstream. The class-switch recombination takes place mainly in the germinal centers of the lymph nodes.

This recombination always takes place starting from IgM and IgD to IgG, IgA and IgE.

It is known that the isotype influences the binding properties of an antibody, i.e. it has an influence on the three-dimensional structure of the antibody. According to the invention, these differences are used for the selection of specific antibodies.

A preferred field of application for the selection of antibodies against CSR-BCRs is that, in addition to the germline version, an IgM version is also provided as part of the selection. Methods for generating BCRs of the IgM type are known in the prior art.

As already mentioned, the present invention provides a method for the production (identification and selection) of biological binding molecules in the form of antibodies or functional fragments thereof, the binding molecules selectively binding to specific epitopes of active or activatable membrane-bound receptors or receptor complexes of B cells, which have already passed through the somatic hypermutation (completely or partially). The selection of the desired binding molecules with selective specificity for the hypermutated BCR regions takes place via a comparative analysis of the binding behavior of binding molecules (candidates) used in the selection approach to a given receptor with hypermutated regions in contrast to the corresponding recombinantly generated receptor in the germline configuration (germline type), which corresponds to the state of the BCR prior to the somatic hypermutation which takes place during the maturation thereof, whereby for the comparative analysis or for the selection both receptor types (hypermutated/germline configuration) are provided as a selection platform in largely native form, i.e. expressed on the surface of suitable B cells (TKO cells in the pre/pro stage). If binding molecules such as, in particular, antibodies against an oligoclonally mixed BCR population are to be selected, a plurality of different BCRs of this population must be used for the selection, the desired antibody being characterized by its specific binding to all BCRs of this population. In other words, a plurality of differently somatically hypermutated B-cell receptors in the form of oligoclonal derivatives of the same origin are used as target receptors in this case.

According to a further embodiment, the selection platform is used not only to identify active and/or activatable receptors or antibodies specifically binding thereto, but also to select antibodies which are able to inactivate an activated BCR or to prevent the activation of a BCR. For this purpose, the antibody to be examined is examined for the binding-specific signal together with an agonist of the BCR (antigen)

(see Example 2). If the BCR delivers a signal after being brought into contact with the agonist, but this is no longer delivered due to a preincubation with an antibody (hybridoma supernatant), the antibody has antagonistic properties. If the BCR signal is extinguished after preincubation with the agonist, the antibody is able to inhibit the conformation-mediated signal transduction. Such an antibody would be a special type of antagonist, since it does not inhibit the antibody-antigen binding, but has a different mechanism of interaction and is therefore able to also inhibit preactivated or constitutively active BCR.

Examples of diseases in which monoclonal or oligoclonal B cells are present include, for example, but not exclusively, leukemias (e.g., CLL) and autoimmune diseases (MS, rheumatoid arthritis, type 1 diabetes, celiac disease).

A cure has so far only been possible through radical destruction of the immune system (with subsequent stem cell transplantation). However, this method is so dangerous that it is only used in very severe cases. An end to the autoimmune reaction (if the autoimmunity persists) can be achieved by completely surgically removing the antigen, which is only possible for organs whose function is dispensable or can be replaced. In type 1 diabetes, the autoimmune reaction itself succeeds in completely eliminating the antigen (insulin-producing β-cells); only the loss of function is treated (through administration of insulin).

The test system is explained in more detail below.

EP 18162676 describes a selection platform for the selection of autonomously active BCR with the help of genetically modified pre/pro B cells (TKO cells). This system allows BCR to be expressed natively in such a way that antibodies against this BCR can be selected with a previously unattained specificity and selectivity. While this system was created for the use of autonomously active BCRs, changes in the application of this system allow an extension to the screening of further BCRs (which do not necessarily have to be autonomously active). Since the selection system is able to select antibodies that differ from the "germline type" in only one point mutation, there is thus the possibility of comprehensively expanding the selection platform, which was previously only designed for autonomously active BCR. While in EP 18162676 the comparison between autonomously active and non-autonomously active BCR is the central element, the present invention relates to the comparison between the BCR after the somatic hypermutation and a genetically engineered "wild type" of the BCR, which corresponds to the BCR before the onset of the hypermutation. The corresponding "wild-type" BCR is generated on the basis of the sequence of the hypermutated BCR. First, the hypermutated BCR is isolated and sequenced and then, based on sequence comparisons with the genomic components of the BCR, a BCR is generated as it was before the somatic hypermutation. This computationally generated sequence is then generated by means of gene synthesis. This synthetic BCR is then also expressed in TKO cells. The comparison of the binding of hybridoma supernatants or, in general, of the antibodies obtained (before or after any purification) makes it possible to identify antibodies that specifically bind to the minimal (but functional) changes that have arisen as a result of the hypermutation. A comparison of germline type versus mutant can be done, for example, by means of flow cytometry. The system is able to recognize minimal differences up to one amino acid difference.

As an example, the generation of an antibody against the R110 mutation of the BCR in CLL demonstrates the method. However, it is also possible to simplify this process and dispense with the controls. Only TKO cells having the somatically hypermutated BCR are then compared with TKO cells of the homologous germline type. However, it is known to a person skilled in the art that such a procedure does not give equally good results as if the method comprised the use of controls.

Individual aspects of the present invention are explained in more detail below on the basis of examples.

EXAMPLE 1

The amino acid sequence of the mutated receptor is known from studies on the genetics of CLL. It consists of two amino acid chains, namely the light chain (LC) and the heavy chain (HC).

```
R110 HC:
                                SEQ ID NO 1
EVQLVESGGGLVKPGGSLRLSCAASGFTFR

SYSMNWVRQAPGKGLEWVSSIISSSSYIYY

ADSVKGRFTISRDNAKNSLYLQMNSLRASD

TALYYCARDQNAMDVWGQGTTVTVSSDSAS

APTLFPLVSCENSPSDTSSVAVGCLAQDFL

PDSITFSWKYKNNSDTSSTRGFPSVLRGGK

YAATSQVLLPSKDVMQGTDEHVVCKVQHPN

GNKEKNVPLPV
R110 LC:
                                SEQ ID NO 02
IRSLEATMAWTVLLLGLLSHCTGSVTSYELT

QPPSVSVAPGKTARITCAGNNIGSKSVHWYQ

QKPGQAPVLVIYYDSDRPSGIPSRFSGSNSG

NTATLTISRVEAGDEADYYCQVWDSGSDHPW

VFGGGTKLTVLSQPKAAPSVTLFPPSSSELQ

ANKATLVCLISDFYPGAVTVAWKADSSPVKA

GVETTTPSKQSNNKYAASSYLSLTPEQWKSH

RSYSCQVTHEGSTVEKTVAPTECS*EFRPS
```

The corresponding germline-type BCR has the sequence

```
WT HC:
                                SEQ ID NO 03
EVQLVESGGGLVKPGGSLRLSCAASGFTFSS

YSMNWVRQAPGKGLEWVSSISSSSSYIYYAD

SVKGRFTISRDNAKNSLYLQMNSLRAEDTAV

YYCARDQNAMDVWGQGTTVTVSSDSASAPTL

FPLVSCENSPSDTSSVAVGCLAQDFLPDSIT

FSWKYKNNSDISSTRGFPSVLRGGKYAATSQ

VLLPSKDVMQGTDEHVVCKVQHPRGNKEKNV

PLPV
WT LC:
                                SEQ ID NO 04
SYVLTQPPSVSVAPGKTARITCGGKNIGSKS

VHWYQQKPGQAPVLVIYYDSDRPSGIPERFS

GSNSGNTATLTISRVEAGDEADYYCQVWDSS
```

-continued

SDHPWVFGGGTKLTVLRQPKAAPSVTLFPPS

SEELQANKATLVCLISDFYPGAVTVAWKADS

SPVKAGVETTTPSKQSNNKYAASSYLSLTPE

QWKSHRSYSCQVTHEGSTVEKTVAPTECS*E

FRPS

In this case, the two sequences differ by more than one amino acid.

The starting point for the production of triple knockout cells (TKO) are transgenic mice, which have, in each case, a knockout for the genes Lambda5, RAG2, and SLP65 (Dühren von Minden et al., 2012, Nature 489, p309-313). The creation of such mice is known to a person skilled in the art and is part of the prior art. To obtain the cells, the bone marrow of the thigh bones was extracted from the mice after they had been sacrificed. The cells obtained in this way were then cultured under conditions which favor the survival of pro/pre B cells (37° C., 7.5% $CO_2$, Iscove's medium, 10% FCS, P/S, murine IL7). After a plurality of passages, a FACS sorting was carried out as a control, the pro/pre B cells were sorted and then cultured. The markers used for this purpose are known to a person skilled in the art.

For the reconstitution with a "BCR of interest," the corresponding sequences coding for the heavy (HC) and light (LC) chains were synthesized and then each cloned into expression vectors containing a CMV promoter. These were introduced into the packaging cell line (Phoenix cell line) by means of lipofection. After incubation for 36 hours, the virus supernatant was removed and used for a spinfection of the TKOs. Both the work to obtain the supernatants and the spinfection of the TKO are widely known methods and known to a person skilled in the art. It should be noted that TKO cells do not necessarily have to be used to carry out the present selection process, since the "knockout" of the SLP65 gene is only required for particular embodiments in which the activation of the receptor is to be detected. In other words, the present technical teaching can also be carried out using cells which each only comprise a "knockout" with regard to the genes RAG2 and Lambda5.

The structural peculiarities of subset-2 B-cell receptors were taken from the relevant literature (see above). Exemplary CLL-R110 $V_H$ and complete LC DNA segments were synthesized by a contract manufacturer in a standard process. These were then fused with a murine IgG1 constant segment by means of PCR and cloned into a CMV vector. The sequence of the finished vector was confirmed by Sanger sequencing.

For the expression of R110 IgG1 (SEQ ID NO 1 and SEQ ID NO 2—R110G is a component of the BCR of type CLL subset 2 (CLL subset 2 is described in the following publications, among others: P. Baliakas et al., 2017, Haematologica 103: e158-e161; B. Stamatopoulos et al., 2018, Clinical cancer research 24.20: 5048-5057)), a human cellular expression system based on HEK293T cells was used. A polyethyleneimine (PEI) based protocol was used for transfection. After a plurality of passages, the supernatant was pooled and the medium contained in the pooled cell supernatant was purified using protein G columns. The purity and quality of the R110 IgG1 was determined by Western blot.

The production of monoclonal antibodies took place according to the standard method in mice and the subsequent generation of hybridoma cells. The screening for positive clones was not carried out using ELISA as is conventional. Since the target structure is a membrane-bound receptor, it is of central importance to also validate the binding of the potential antibodies in a cellular system, i.e. while largely preserving the cell physiological conditions that are native to this cell type. First, groups of pooled supernatants were examined for binding events by means of FACS analysis. For this purpose, different CLL-R110 BCR variants were expressed on the surface of a cell line (TKO) which itself cannot express a BCR. In this way it was first possible to identify the supernatants, the antibodies of which showed binding. The supernatants of the individual hybridoma clones were then examined in more detail with regard to their binding in order to identify highly specific clones with high affinity in this way.

For the screening method, different vectors for the following combinations of heavy chain (HC) and light chain (LC) of the corresponding CLL-BCRs were used in the course of the previous transformation, these combinations being used on the surface of the BCR reconstitution system:
  Control (transformation vector without BCR)
  Vector with DNA coding for the CLL-R110G BCR
  Vector with DNA coding for the germline-type BCR to R110G
  Vector with HC/germline-type LC typical for the CLL-R110G In the 1st selection round, supernatants from a plurality of clones were combined and examined with regard to their binding profile to the selection matrix. A positive binding profile is given when a specific binding to the "BCR of interest" is shown. Groups showing such a profile were isolated and the binding profile of the individual clones was characterized again on the selection matrix in a second selection round. The binding of the monoclonal antibodies was verified using a FACS binding assay using a fluorescence-labeled anti-mouse IgG antibody, using different B cells with the following specificity: A) no BCR (control); B) a CLL-R110G BCR; C) a germline-type BCR to CLL-R110G; D) a BCR with a CLL-R110G-typical heavy chain and light chain of the germline type to CLL-R110G.

Based on the finding that the antibody only binds to cells with the target structures (CLL-R110G BCR), it can be concluded that an antibody is present in this case that specifically binds to cells with the mutated receptor.

It was shown that the use of cells that are in the pro/pre stage of B-cell development is necessary for the exact expression of the BCR required for detection. These cells are developed in order to represent new BCRs by precisely folding and expressing them on their surface. The inactivation (knockout) of RAG2 and Lambda5 prevents the expression of an endogenous BCR or pre BCR. The deletion of SLP65 and the subsequent reconstruction of an inducible SLP65 make it possible to characterize the level of activity of the "BCR of Interest," which can be done, for example, by adding an antigen.

To determine the amino acid sequence of the monoclonal antibodies selected by means of selection, the mRNA was isolated from the individual hybridoma clones, cDNA was generated from it and this was amplified using anchor PCR (Rapid expression cloning of human immunoglobulin Fab fragments for the analysis of antigen specificity of B cell lymphomas and anti-idiotype lymphoma vaccination; Osterroth F, Alkan O, Mackensen A, Lindemann A, Fisch P, Skerra A, Veelken H., J Immunol Methods 1999 Oct. 29; 229 (1-2): 141-53).

After identification and sequence determination of the regions (CDRs) important for binding, these were transferred to a human antibody scaffold by means of PCR. For this purpose, the $V_H$ sequence was generated in silico from the human FR regions and the murine CDR regions and then synthesized as DNA fragments. These were then fused with a human IgG1 by means of PCR and cloned into a vector suitable for expression.

In addition to the complete immunoglobulins, synthetic peptides were also used to generate the monoclonal antibodies, which represented the regions for the ability of an autonomous signal.

The specific monoclonal antibody against R110G BCR was sequenced. The following amino acid sequences were determined, SEQ ID NO. 5 relating to the variable part of the heavy chain (HC), and SEQ ID NO. 6 relating to the variable part of the light chain (LC), and the marked regions—in the order given—denote CDR 1, 2 and 3.

```
(AVA-mAB01 HC)
                                    SEQ ID NO. 5
QVQLQQSGPGLVQPSQSLSITCTVSGFSLTSYGIHW

VRQSPGKGLEWLGVIWRGGGTDSNAAFMSRLSITKD

NSKSQVFFKMNSLQADDTAIYYCARSRYDEEESMNY

WGQGTSVTVSS (AVA-mAb01 LC)
                                    SEQ ID NO. 6
QIVLTQSPASLSASVGETVTITCRASGNIHSYLAW

YQQKQGKSPQLLVYNAKTLADGVPSRFSGSGSGTQ

YSLKINSLQPEDFGSYYCQHFWNTPPTFGAGTKLE

LK
```

The partial sequences of the heavy chain corresponding to CDR1, CDR2, and CDR3 according to SEQ ID NO. 5 are indicated in SEQ ID NOS. 7 to 9, while the partial sequences of the light chain corresponding to CDR1, CDR2, and CDR3 are shown according to SEQ ID NO. 6 in SEQ ID NOS. 10 to 12.

```
(AVA-mAB01 CDR1 HC)
                                    SEQ ID NO. 7
GFSLTSYG (AVA-mAB01 CDR2 HC)
                                    SEQ ID NO. 8
IWRGGGT (AVA-mAB01 CDR3 HC)
                                    SEQ ID NO. 9
ARSRYDEEESMNY (AVA-mAB01 CDR1 LC)
                                    SEQ ID NO. 10
GNIHSY (AVA-mAB01 CDR2 LC)
                                    SEQ ID NO. 11
NAKT (AVA-mAB01 CDR3 LC)
                                    SEQ ID NO. 12
QHFWNTPPT
```

EXAMPLE 2

The same hybridomas as in Example I were used. Only the method of selection differs. In this case, the selection took place using TKO cells which had previously been incubated for exposure to the BCR antigen (5 µg/ml, 5 minutes). This caused the antigen to bind to the BCR. An activation of the BCR (with possible internalization of the BCR) does not take place because SLP65 has not yet been induced. The cells were then divided. One part was measured in a BD Fortessa II FACS device to carry out a functionality check. This device allows the measurement to be interrupted and resumed with new parameters. Most other FACS devices do not allow this operation. For this purpose, the cells were incubated for 45 minutes before the measurement with Indo-1 according to the manufacturer's instructions. In the event of calcium influx into the cell, Indo-1 generates a fluorescence signal that can then be measured by the FACS device. The cells were measured for one minute to create a baseline. Subsequently, 4-OH tamoxifen was added (2 mM), whereby the signal transduction of the BCR was reconstituted, and a calcium signal could be detected. This calcium signal indicated the activation of the BCR. In order to detect activation (or inactivation) in a BCR, the calcium signal of the activatable receptor (in cells with a reconstituted calcium signal) had to be compared with the signal of the same BCR in cells without a reconstituted calcium signal. The Ca signal before and after activation was compared with the agonist. After the activation of the cells could be detected, the second batch of cells (without 4-OHT activation) was now used to select a suitable antibody against the activated BCR (see Example 1). If the then selected antibody does not bind to non-activated BCR, an antibody which only binds to active BCR has been selected successfully.

Example III

The cells were then incubated with the potential inhibitor before the stimulation (5 µg/ml, 5 minutes). These cells were then stimulated with the agonist (antigen, see Example 2) (or, in the case of autonomously active cells, used without stimulation, since the stimulant is on the cell itself), and the Ca signal after the inhibition with the inhibitor was compared with the Ca signal of the cells without inhibitor. An inhibition meant that the CA signal of the cells with the inhibitor was significantly lower (at least 50% of the net comparison signal).

The following were used for screening in this case: (induced means that these cells were previously treated with hydroxy tamoxifen)
    Induced control (transformation vector without BCR)
    Induced cells: Transformed with vector with DNA coding for the CLL-R110G BCR 1
    Induced cells: Transformed with vector with DNA coding for the germline-type BCR to form R110G In the case of BCRs that are not autonomously active, the step of preincubation with the agonist was also required. Otherwise the same approaches were used.

---

The invention claimed is:

1. A method for selecting a biological binding molecule which specifically binds to a somatically hypermutated B-cell receptor as the target receptor, but not to a homologous, non-hypermutated B-cell receptor, in a cell-based system using immature B cells, which are in the pro/pre stage, comprising the following steps:
   (a) providing a plurality of biological binding molecules obtained by immunizing a mammal with B-cell receptors or their fragments and then immortalizing and purifying them;
   (b) providing immature B cells in the pro/pre stage, which are not able to express the native genes for RAG2 and/or RAG1 as well as Lambda5, but which have been enabled to express somatically hypermutated B-cell receptors as target receptors on their cell surface;
   (c) providing immature B cells in the pro/pre stage, which are not able to express the native genes for RAG2 and/or RAG1 as well as Lambda5, but which have been enabled to express recombinantly produced B-cell receptors on their cell surface, which are homologous receptors compared to the receptors according to (b), but not having hypermutated regions, as reference receptors;
   (d) comparatively identifying and analyzing the binding behavior of the binding molecules provided according to step (a) with respect to cells that are provided according to steps (b) and (c);
   (e) selecting at least one binding molecule which specifically binds to cells provided according to step (b), but not to cells provided according to step (c).

2. The method according to claim 1, characterized in that the target receptor is an activatable B-cell receptor.

3. The method according to claim 2, characterized in that a plurality of differently somatically hypermutated B-cell receptors in the form of oligoclonal derivatives of the same origin are used as target receptors.

4. The method according to claim 2, characterized in that the target receptor was previously activated with an antigen.

5. The method according to claim 4, characterized in that the successful activation was confirmed before the selection.

6. The method according to claim 1, characterized in that the cells provided according to steps (b) and (c) are additionally unable to express the native gene for SLP65.

7. The method according to claim 6, characterized in that step (e), in addition to determining a specific binding of the binding molecule to cells provided according to step (b), includes a confirmation by an activity measurement after induction of SLP65.

8. The method according to claim 6, characterized in that a plurality of differently somatically hypermutated B-cell receptors in the form of oligoclonal derivatives of the same origin are used as target receptors.

9. The method according to claim 6, characterized in that the target receptor was previously activated with an antigen.

10. The method according to claim 9, characterized in that the successful activation was confirmed before the selection.

11. The method according to claim 1, characterized in that a plurality of differently somatically hypermutated B-cell receptors in the form of oligoclonal derivatives of the same origin are used as target receptors.

12. The method according to claim 11, characterized in that the target receptor was previously activated with an antigen.

13. The method according to claim 12, characterized in that the successful activation was confirmed before the selection.

14. The method according to claim 1, characterized in that the target receptor was previously activated with an antigen.

15. The method according to claim 14, characterized in that the successful activation was confirmed before the selection.

* * * * *

SEQUENCE LISTING

<160> NUMBER OF SEQ ID NOS: 12

<210> SEQ ID NO 1
<211> LENGTH: 218
<212> TYPE: PRT
<213> ORGANISM: Homo sapiens

<400> SEQUENCE: 1

-continued

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Ser Met Asn Trp Val Arg Gln Ala Pro Gly Lys Gly Leu Glu Trp Val
        35                  40                  45

Ser Ser Ile Ile Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Arg Asp Gln Asn Ala Met Asp Val Trp Gly Gln Gly Thr Thr Val
        100                 105                 110

Thr Val Ser Ser Asp Ala Pro Thr Leu Phe Pro Leu Val Ser Cys Glu
    115                 120                 125

Asn Ser Pro Ser Asp Thr Ser Ser Val Ala Val Gly Cys Leu Ala Gln
    130                 135                 140

Asp Phe Leu Pro Asp Ser Ile Thr Phe Ser Trp Lys Tyr Lys Asn Asn
145                 150                 155                 160

Ser Asp Ile Ser Ser Thr Arg Gly Phe Pro Ser Val Leu Arg Gly Gly
            165                 170                 175

Lys Tyr Ala Ala Thr Ser Gln Val Leu Leu Pro Ser Lys Asp Val Met
        180                 185                 190

Gln Gly Thr Asp Glu His Val Val Cys Lys Val Gln His Pro Asn Gly
    195                 200                 205

Asn Lys Glu Lys Asn Val Pro Leu Pro Val
210                 215

<210> SEQ ID NO 2
<211> LENGTH: 246
<212> TYPE: PRT
<213> ORGANISM: Homo sapiens

<400> SEQUENCE: 2

Ile Arg Ser Leu Glu Ala Thr Met Ala Trp Thr Val Leu Leu Leu Gly
1               5                   10                  15

Leu Leu Ser His Cys Thr Gly Ser Val Thr Ser Tyr Glu Leu Thr Gln
            20                  25                  30

Pro Pro Ser Val Ser Val Ala Pro Gly Lys Thr Ala Arg Ile Thr Cys
        35                  40                  45

Ala Gly Asn Asn Ile Gly Ser Lys Ser Val His Trp Tyr Gln Gln Lys
    50                  55                  60

Pro Gly Gln Ala Pro Val Leu Val Ile Tyr Tyr Asp Ser Asp Arg Pro
65                  70                  75                  80

Ser Gly Ile Pro Glu Arg Phe Ser Gly Ser Asn Ser Gly Asn Thr Ala
            85                  90                  95

Thr Leu Thr Ile Ser Arg Val Glu Ala Gly Asp Glu Ala Asp Tyr Tyr
        100                 105                 110

Cys Gln Val Trp Asp Ser Gly Ser Asp His Pro Trp Val Phe Gly Gly
    115                 120                 125

Gly Thr Lys Leu Thr Val Leu Arg Gln Pro Lys Ala Ala Pro Ser Val
130                 135                 140

Thr Leu Phe Pro Pro Ser Ser Glu Glu Leu Gln Ala Asn Lys Ala Thr

```
                145                 150                 155                 160
Leu Val Cys Leu Ile Ser Asp Phe Tyr Pro Gly Ala Val Thr Val Ala
                165                 170                 175

Trp Lys Ala Asp Ser Ser Pro Val Lys Ala Gly Val Glu Thr Thr Thr
                180                 185                 190

Pro Ser Lys Gln Ser Asn Asn Lys Tyr Ala Ala Ser Ser Tyr Leu Ser
                195                 200                 205

Leu Thr Pro Glu Gln Trp Lys Ser His Arg Ser Tyr Ser Cys Gln Val
210                 215                 220

Thr His Glu Gly Ser Thr Val Glu Lys Thr Val Ala Pro Thr Glu Cys
225                 230                 235                 240

Ser Glu Phe Arg Pro Ser
                245

<210> SEQ ID NO 3
<211> LENGTH: 221
<212> TYPE: PRT
<213> ORGANISM: Homo sapiens

<400> SEQUENCE: 3

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
                35                  40                  45

Ser Ser Ile Ser Ser Ser Ser Ser Tyr Ile Tyr Tyr Ala Asp Ser Val
                50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Asn Ala Met Asp Val Trp Gly Gln Gly Thr Thr Val
                100                 105                 110

Thr Val Ser Ser Asp Ser Ala Ser Ala Pro Thr Leu Phe Pro Leu Val
                115                 120                 125

Ser Cys Glu Asn Ser Pro Ser Asp Thr Ser Ser Val Ala Val Gly Cys
                130                 135                 140

Leu Ala Gln Asp Phe Leu Pro Asp Ser Ile Thr Phe Ser Trp Lys Tyr
145                 150                 155                 160

Lys Asn Asn Ser Asp Ile Ser Ser Thr Arg Gly Phe Pro Ser Val Leu
                165                 170                 175

Arg Gly Gly Lys Tyr Ala Ala Thr Ser Gln Val Leu Leu Pro Ser Lys
                180                 185                 190

Asp Val Met Gln Gly Thr Asp Glu His Val Val Cys Lys Val Gln His
                195                 200                 205

Pro Asn Gly Asn Lys Glu Lys Asn Val Pro Leu Pro Val
                210                 215                 220

<210> SEQ ID NO 4
<211> LENGTH: 220
<212> TYPE: PRT
<213> ORGANISM: Homo sapiens

<400> SEQUENCE: 4

Ser Tyr Val Leu Thr Gln Pro Pro Ser Val Ser Val Ala Pro Gly Lys
```

```
                1               5                      10                      15
            Thr Ala Arg Ile Thr Cys Gly Gly Asn Asn Ile Gly Ser Lys Ser Val
                            20                      25                      30
            His Trp Tyr Gln Gln Lys Pro Gly Gln Ala Pro Val Leu Val Ile Tyr
                            35                      40                      45
            Tyr Asp Ser Asp Arg Pro Ser Gly Ile Pro Glu Arg Phe Ser Gly Ser
                50                      55                      60
            Asn Ser Gly Asn Thr Ala Thr Leu Thr Ile Ser Arg Val Glu Ala Gly
            65                      70                      75                      80
            Asp Glu Ala Asp Tyr Tyr Cys Gln Val Trp Asp Ser Ser Ser Asp His
                            85                      90                      95
            Pro Trp Val Phe Gly Gly Gly Thr Lys Leu Thr Val Leu Arg Gln Pro
                            100                     105                     110
            Lys Ala Ala Pro Ser Val Thr Leu Phe Pro Pro Ser Ser Glu Glu Leu
                            115                     120                     125
            Gln Ala Asn Lys Ala Thr Leu Val Cys Leu Ile Ser Asp Phe Tyr Pro
                            130                     135                     140
            Gly Ala Val Thr Val Ala Trp Lys Ala Asp Ser Ser Pro Val Lys Ala
            145                     150                     155                     160
            Gly Val Glu Thr Thr Thr Pro Ser Lys Gln Ser Asn Asn Lys Tyr Ala
                            165                     170                     175
            Ala Ser Ser Tyr Leu Ser Leu Thr Pro Glu Gln Trp Lys Ser His Arg
                            180                     185                     190
            Ser Tyr Ser Cys Gln Val Thr His Glu Gly Ser Thr Val Glu Lys Thr
                            195                     200                     205
            Val Ala Pro Thr Glu Cys Ser Glu Phe Arg Pro Ser
                            210                     215                     220

<210> SEQ ID NO 5
<211> LENGTH: 119
<212> TYPE: PRT
<213> ORGANISM: Homo sapiens

<400> SEQUENCE: 5

Gln Val Gln Leu Gln Gln Ser Gly Pro Gly Leu Val Gln Pro Ser Gln
            1               5                      10                      15
            Ser Leu Ser Ile Thr Cys Thr Val Ser Gly Phe Ser Leu Thr Ser Tyr
                            20                      25                      30
            Gly Ile His Trp Val Arg Gln Ser Pro Gly Lys Gly Leu Glu Trp Leu
                            35                      40                      45
            Gly Val Ile Trp Arg Gly Gly Thr Asp Ser Asn Ala Ala Phe Met
                50                      55                      60
            Ser Arg Leu Ser Ile Thr Lys Asp Asn Ser Lys Ser Gln Val Phe Phe
            65                      70                      75                      80
            Lys Met Asn Ser Leu Gln Ala Asp Asp Thr Ala Ile Tyr Tyr Cys Ala
                            85                      90                      95
            Arg Ser Arg Tyr Asp Glu Glu Glu Ser Met Asn Tyr Trp Gly Gln Gly
                            100                     105                     110
            Thr Ser Val Thr Val Ser Ser
                            115

<210> SEQ ID NO 6
<211> LENGTH: 107
<212> TYPE: PRT
<213> ORGANISM: Homo sapiens
```

```
<400> SEQUENCE: 6

Gln Ile Val Leu Thr Gln Ser Pro Ala Ser Leu Ser Ala Ser Val Gly
1               5                   10                  15

Glu Thr Val Thr Ile Thr Cys Arg Ala Ser Gly Asn Ile His Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Asn Thr Pro Pro
                85                  90                  95

Thr Phe Gly Ala Gly Thr Lys Leu Glu Leu Lys
            100                 105

<210> SEQ ID NO 7
<211> LENGTH: 8
<212> TYPE: PRT
<213> ORGANISM: Homo sapiens

<400> SEQUENCE: 7

Gly Phe Ser Leu Thr Ser Tyr Gly
1               5

<210> SEQ ID NO 8
<211> LENGTH: 7
<212> TYPE: PRT
<213> ORGANISM: Homo sapiens

<400> SEQUENCE: 8

Ile Trp Arg Gly Gly Gly Thr
1               5

<210> SEQ ID NO 9
<211> LENGTH: 13
<212> TYPE: PRT
<213> ORGANISM: Homo sapiens

<400> SEQUENCE: 9

Ala Arg Ser Arg Tyr Asp Glu Glu Ser Met Asn Tyr
1               5                   10

<210> SEQ ID NO 10
<211> LENGTH: 6
<212> TYPE: PRT
<213> ORGANISM: Homo sapiens

<400> SEQUENCE: 10

Gly Asn Ile His Ser Tyr
1               5

<210> SEQ ID NO 11
<211> LENGTH: 4
<212> TYPE: PRT
<213> ORGANISM: Homo sapiens

<400> SEQUENCE: 11

Asn Ala Lys Thr
1
```

```
<210> SEQ ID NO 12
<211> LENGTH: 9
<212> TYPE: PRT
<213> ORGANISM: Homo sapiens

<400> SEQUENCE: 12

Gln His Phe Trp Asn Thr Pro Pro Thr
1               5
```